US005800526A

United States Patent [19]
Anderson et al.

[11] Patent Number: 5,800,526
[45] Date of Patent: Sep. 1, 1998

[54] MULTI-ANCHOR STENT

[75] Inventors: Scott C. Anderson, Sunnyvale; Peter S. Brown, Mountain View; Geoffrey A. Orth, La Granada, all of Calif.

[73] Assignee: EndoTex Interventional Systems, Inc., Menlo Park, Calif.

[21] Appl. No.: 901,226

[22] Filed: Jul. 24, 1997

Related U.S. Application Data

[63] Continuation of Ser. No. 757,486, Nov. 27, 1996, abandoned, which is a continuation of Ser. No. 404,488, Mar. 17, 1995, abandoned.

[51] Int. Cl.$^6$ ............................................. A61F 2/06
[52] U.S. Cl. .................. 623/1; 623/12; 606/198; 606/194; 606/191
[58] Field of Search ................... 623/1, 11, 12; 606/108, 191, 194, 195, 198; 138/108, 112; 411/61, 71, 74

[56] References Cited

U.S. PATENT DOCUMENTS

| | | |
|---|---|---|
| 3,657,744 | 4/1972 | Ersek . |
| 3,993,078 | 11/1976 | Bergentz et al. . |
| 4,140,126 | 2/1979 | Choudhury . |
| 4,441,215 | 4/1984 | Kaster ............................ 604/49 |
| 4,560,374 | 12/1985 | Hammerslag ................... 604/49 |
| 4,562,596 | 1/1986 | Kornberg ......................... 623/1 |
| 4,580,568 | 4/1986 | Gianturco ....................... 604/96 |
| 4,733,665 | 3/1988 | Palmaz ............................ 623/1 |
| 4,739,762 | 4/1988 | Palmaz ............................ 623/1 |
| 4,740,207 | 4/1988 | Kreamer ......................... 623/1 |
| 4,776,337 | 10/1988 | Palmaz ............................ 623/1 |
| 4,787,899 | 11/1988 | Lazarus .......................... 623/1 |
| 4,793,348 | 12/1988 | Palmaz . |

(List continued on next page.)

FOREIGN PATENT DOCUMENTS

| | | |
|---|---|---|
| 0 177 330 B1 | 6/1991 | European Pat. Off. . |
| 0 461 791 A1 | 12/1991 | European Pat. Off. . |
| 0 479 557 A1 | 4/1992 | European Pat. Off. . |
| 0 480 667 A1 | 4/1992 | European Pat. Off. . |
| 0 539 237 A1 | 4/1993 | European Pat. Off. . |
| 0 565 251 A1 | 10/1993 | European Pat. Off. . |
| 2 164 562 | 3/1986 | United Kingdom . |
| WO 90/15582 | 12/1990 | WIPO . |

OTHER PUBLICATIONS

U.S. Application Serial No. 08/340,112 filed Nov. 15, 1994 entitled Intraluminal Stent For Attaching A Graft.

"Transluminal Expandable Nitinol Coil Stent Grafting: Preliminary Report," by Charles T. Dotter, M.D., et al., in *Technical Developments and Instrumentation*, Apr. 1983, pp. 259–260.

"Nonsurgical Placement of Arterial Endoprostheses: A New Technique Using Nitinol Wire," by Andrew Cragg, M.D., et al., Apr. 1983, pp. 261–263.

"Radiological Follow–Up of Transluminally Inserted Vascular Endoprostheses: An Experimental Study Using Expanding Spirals," by D. Maass, et al., in *Radiology*, Sep. 1984, pp. 659–663.

"Expandable Intraluminal Vascular Graft: A Feasibility Study," by Julio C. Palmaz, M.D., et al., In *Surgery*, vol. 99, No. 2, pp. 199–205, Feb. 1986.

(List continued on next page.)

*Primary Examiner*—Randy C. Shay
*Attorney, Agent, or Firm*—Fish & Neave; Nicola A. Pisano

[57] ABSTRACT

The intravascular multi-anchor stent includes a plurality of cylindrical elements that are independently expandable in the radial direction and that are interconnected so as to be generally aligned on a common longitudinal axis, and a plurality of barbs along the entire circumference of the stent that face outwardly when the stent is in an expanded condition. A plurality of connecting elements are provided for interconnecting only the cylindrical elements that are adjacent to each other so that the stent, when expanded in the radial direction, retains its overall length without appreciable shortening.

10 Claims, 8 Drawing Sheets

U.S. PATENT DOCUMENTS

| | | | |
|---|---|---|---|
| 4,800,882 | 1/1989 | Gianturco | 623/13 |
| 4,848,343 | 7/1989 | Wallsten et al. | 604/96 |
| 4,856,516 | 8/1989 | Hillstad | 623/1 |
| 4,892,539 | 1/1990 | Koch | 623/1 |
| 4,907,336 | 3/1990 | Gianturco | 128/899 |
| 4,994,071 | 2/1991 | MacGregor | 606/194 |
| 5,035,706 | 7/1991 | Gianturco et al. | 606/198 |
| 5,041,126 | 8/1991 | Gianturco | 606/195 |
| 5,078,726 | 1/1992 | Kreamer | 606/194 |
| 5,102,417 | 4/1992 | Palmaz | 606/195 |
| 5,104,399 | 4/1992 | Lazarus | 623/1 |
| 5,116,365 | 5/1992 | Hillstead | 623/1 |
| 5,133,732 | 7/1992 | Wiktor | 612/1 |
| 5,135,536 | 8/1992 | Hillstead | 623/1 |
| 5,156,619 | 10/1992 | Ehrenfeld | 623/1 |
| 5,158,548 | 10/1992 | Lau et al. | 604/96 |
| 5,161,547 | 11/1992 | Tower | 128/898 |
| 5,178,618 | 1/1993 | Kandarpa | 606/28 |
| 5,207,695 | 5/1993 | Trout, III | 606/198 |
| 5,211,658 | 5/1993 | Clouse | 606/191 |
| 5,211,683 | 5/1993 | Maginot | 623/1 |
| 5,219,355 | 6/1993 | Parodi et al. | 606/191 |
| 5,226,913 | 7/1993 | Pinchuk | 623/1 |
| 5,242,399 | 9/1993 | Lau et al. | 604/104 |
| 5,256,150 | 10/1993 | Quiachon et al. | 604/171 |
| 5,263,963 | 11/1993 | Garrison et al. | 606/198 |
| 5,275,622 | 1/1994 | Lazarus et al. | 623/1 |
| 5,282,824 | 2/1994 | Gianturco | 623/1 |
| 5,304,200 | 4/1994 | Spaulding | 623/1 |
| 5,304,220 | 4/1994 | Maginot | 623/1 |
| 5,314,472 | 5/1994 | Fontaine | 623/1 |
| 5,330,528 | 7/1994 | Lazim | 623/1 |
| 5,342,387 | 8/1994 | Summers | 606/198 |
| 5,344,426 | 9/1994 | Lau et al. | 623/1 |
| 5,354,308 | 10/1994 | Simon et al. | 623/1 |
| 5,360,401 | 11/1994 | Turnland | 604/96 |
| 5,397,355 | 3/1995 | Marin et al. | 623/12 |
| 5,514,154 | 5/1996 | Lau et al. | 606/195 |
| 5,591,197 | 1/1997 | Orth et al. | 623/12 |

OTHER PUBLICATIONS

"Percutaneous Endovascular Stents: An Experimental Evaluation," by Kenneth C. Wright, Ph.D., et al., in *Radiology*, Jul. 1985, pp. 69–72.

"Atherosclerotic Rabbit Aortas: Expandable Intraluminal Grafting," by Julio C. Palmaz, M.D., et al., in *Radiology*, Sep. 1986 pp. 723–726.

"Percutaneous Endovascular Graft: Experimental Evaluation," by David D. Lawrence, Jr., M.D., et al., in *Radiology* May, 1987, pp. 357–360.

"Balloon Expandable Intracoronary Stents in the Adult Dog," by Richard A. Schatz, M.D., et al., in *Circulation*, vol. 76, No. 2, 1987, pp. 450–457.

"Implantation of Balloon–Expandable Intravascular Grafts by Catheterization in Pulmonary Arteries and Systemic Veins," by Charles E. Mullins, M.D., et al., in *Circulation*, vol. 77, No. 1, Jan. 1988, pp. 188–199.

"Elastic Characteristics of the Self–Expanding Metallic Stents," by B. G. Fallone, Ph.D., et al., Investigative Radiology, vol. 23, May 1988, pp. 370–376.

"Balloon–Expandable Intravascular Stent," by Julio C. Palmaz, M.D., in AJR 150, Jun. 1988, pp. 1263–1269.

"Self–Expanding Endovascular Graft: An Experimental Study in Dogs," by Tetsuya Yoshioka, et al., in AJR, 151, Oct. 1988, pp. 673–676.

"Transfemoral Intraluminal Graft Implanation for Abdominal Aortic Aneurysms," by J.C. Parodi, M.D., et al., in *Annals of Vascular Surgery*, vol. 5, No. 6, pp. 491–499.

"Intraluminal Bypass of Abdominal Aortic Aneurysm: Feasibility Study," by Jean Claude Laborde, M.D., et al., in RSNA, Jul. 1992.

"Transfemoral Endovascular Aortic Graft Placement," by Timothy A.M. Chuter, BM, BS et al., in *Journal of Vascular Surgery*, vol. 18, No. 2, Aug. 1993, pp. 185–197.

"Endovascular Grafts," by Darwin Eton, M.D., FACS, University of Illinois at Chicago, Mar. 1994 pp. 1–28.

"Transfemoral Endoluminal Repair of Abdominal Aortic Aneurysm With Bifurcated Graft," by S.W. Yusuf, et al., in *The Lancet*, vol. 344, Sep. 3, 1994, pp. 650–652.

U.S. Patent Application Serial No. 08/175,214, filed Dec. 28, 1993, entitled Expandable Stents And Method For Making Same (with drawing figures).

U.S. Divisional Application Serial No. 08/214,402, filed Mar. 17, 1994, entitled Expandable Stents And Method For Making Same (with drawing figures).

U.S. Continuation–in–Part Application Serial No. 08/281,790, filed Jul. 28, 1994, entitled Expandable Stents And Method For Making Same (with drawing figures).

FIG. 2
FIG. 3
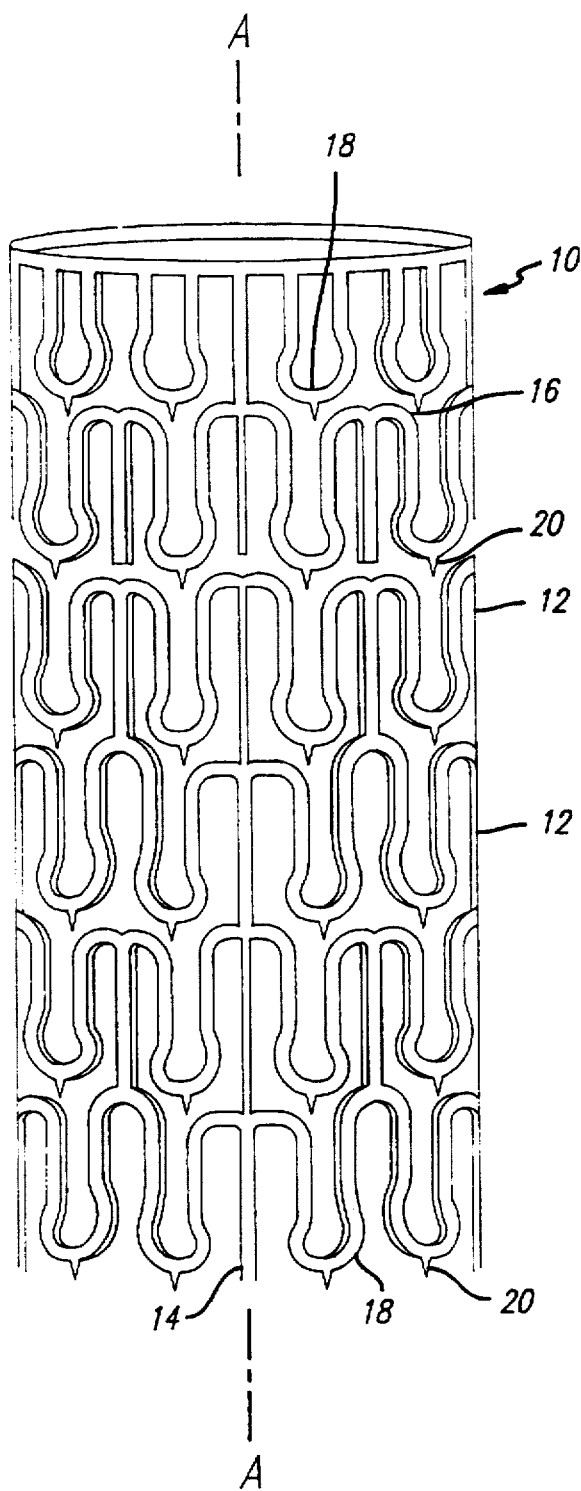
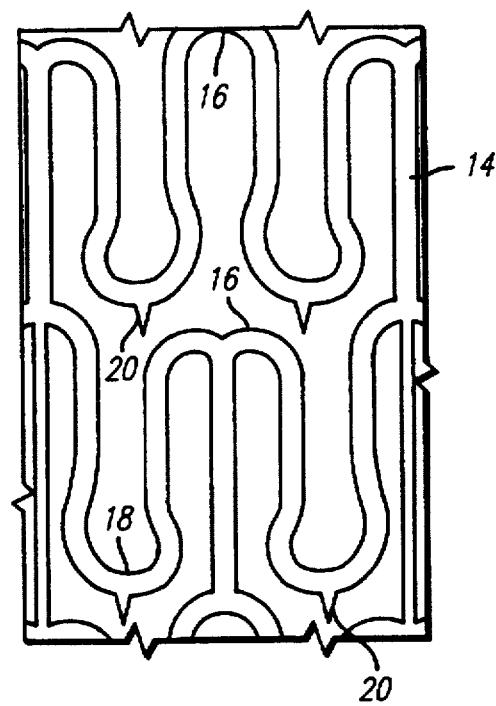

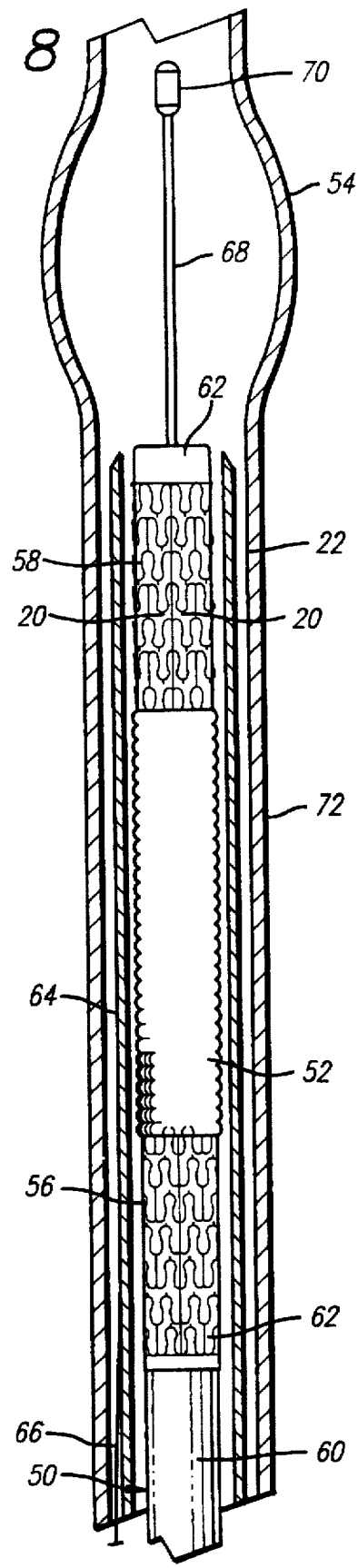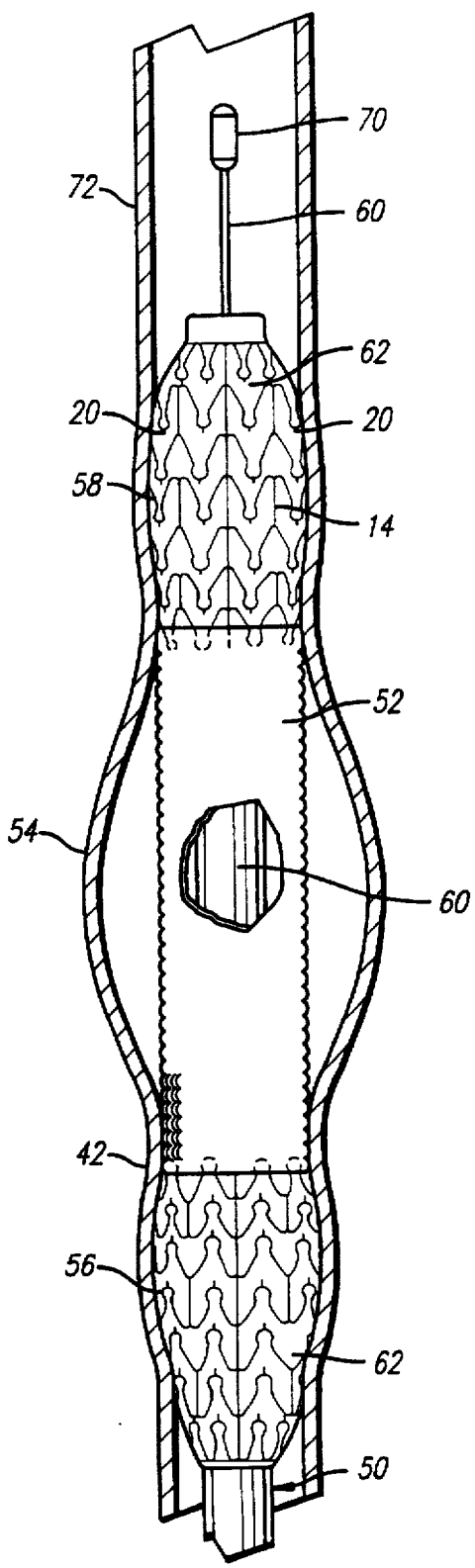

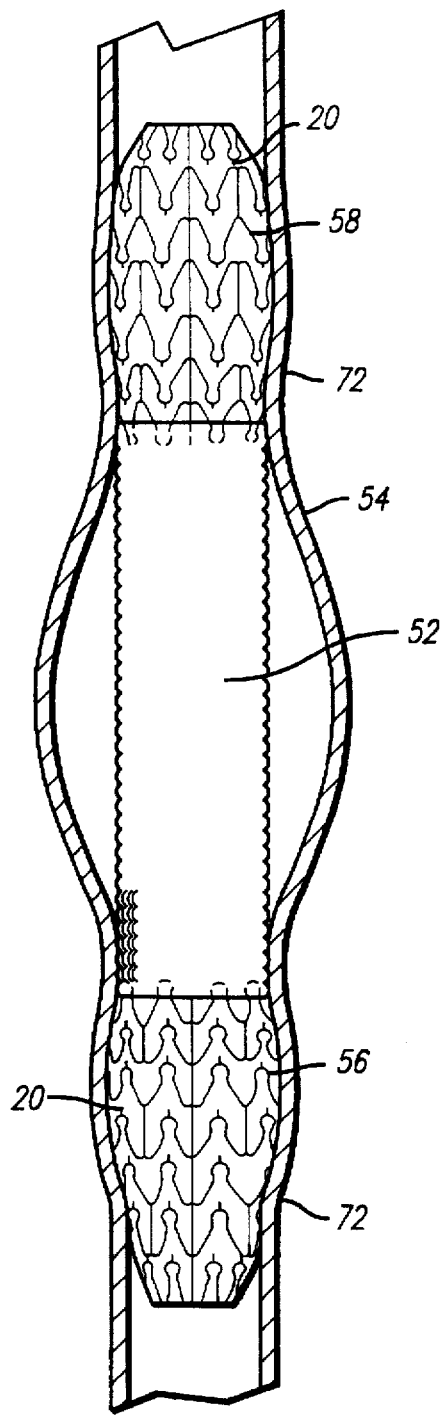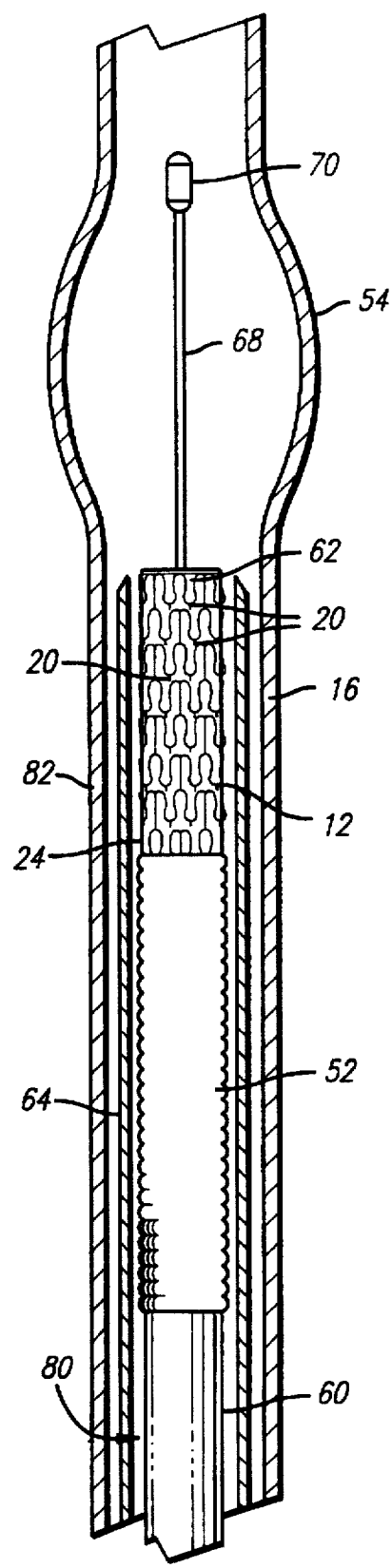

FIG. 12
FIG. 13
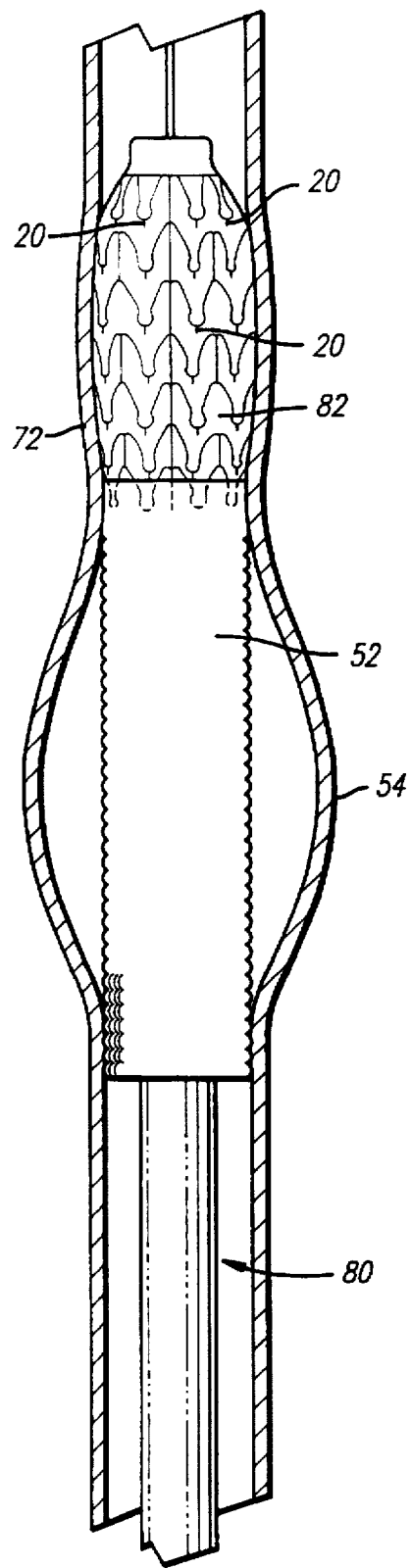
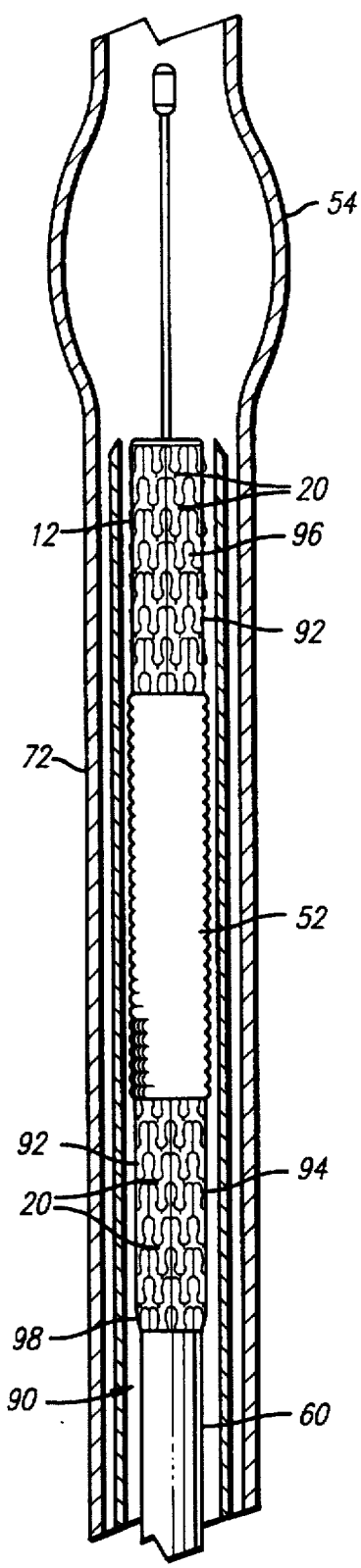

MULTI-ANCHOR STENT

This is a continuation of application Ser. No. 08/757,486, filed Nov. 27, 1996, now abandoned, entitled MULTI-ANCHOR STENT, which is a continuation of U.S. patent application Ser. No. 08/404,488, filed Mar. 17, 1995, now abandoned.

BACKGROUND OF THE INVENTION

1. Field of the Invention

This invention relates generally to endoprostheses, and more particularly concerns intraluminal grafts and stents for placement in an area of a body lumen that has been weakened by damage or disease, such as by aneurysm of the abdominal aorta.

2. Description of Related Art

An abdominal aortic aneurysm ("AAA") is an abnormal dilation of the arterial wall of the aorta in the region of the aorta that passes through the abdominal cavity. The condition most commonly results from atherosclerotic disease. Frequently, abdominal aortic aneurysms are dissecting aneurysms that are formed when there is a tear or fissure in the arterial lining or wall through which blood is forced and where it eventually clots, forming a thrombosis that swells and weakens the vessel. Abdominal aortic aneurysms do not cause pain, but are easily detected in a thorough physical examination. If the aneurysm is not detected and treated, it is likely to rupture and cause massive hemorrhaging fatal to the patient.

Treatment of AAAs typically takes the form of arterial reconstructive surgery. One such method is bypass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Nylons and synthetic fibers such as those manufactured under the trademarks DACRON or TEFLON have been found to be suitable for the construction of the graft. Studies have shown that the mortality rate associate with this surgical procedure is favorable (less than 5%) when it is performed prior to rupture of an aneurysm. However, patients having an AAA are typically over 65 year of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Another procedure developed as an alternative to conventional surgical methods involves placement of a graft at the site of the aneurysm. However, the graft is deployed there by being routed through the vascular system carried by a catheter, wire or other device suitable for negotiating the vasculature. The graft and its deployment system often are introduced into the blood stream percutaneously with a femoral approach and the entire procedure can be performed using local rather than general anesthesia. Once the graft has been positioned at the aneurysm, it is disengaged from the delivery system and can be affixed to the aortic wall both distally and proximally of the aneurysm. For this purpose, grafting systems usually include fixation means such as staples or hooks which can be manipulated and driven into the intima of the vessel via some mechanical feature of the system, or by some physical process, such as expansion of the graft through application of pressure or temperature change. To avoid premature detachment of the graft and to prevent the attachment elements from damaging the vessels or halting the forward movement of the system while the graft is being routed to the treatment site, the systems often are provided with a feature such as a capsule or a sheath that protects and contains the graft until such time as deployment is desired.

Once the graft is in place, it is positioned in the vessel spanning the site of the aneurysm such that the walls of the graft are generally parallel to the walls of the affected area of the aorta. The aneurysm thus is excluded from the circulatory system by the graft rather than being resected altogether.

Grafting systems are known that include what is commonly referred to as an attachment system for deploying the graft. The attachment system is typically a tubular device which is fitted inside and is generally coaxial with the graft, and can extend beyond either or both of the proximal and distal ends of the graft. The attachment system often has a lattice-like or open weave structure, which provides it with flexibility and which promotes rapid endothelial tissue growth through the structure once the graft has been deployed. It may be provided with additional hook-like elements for penetration of the intimal walls for attachment of the graft to the aorta, or those hook-like elements may be provided on the graft itself. Graft systems of the type described can be found in U.S. Pat. Nos. 4,787,899; 5,104,399; 5,219,355; and 5,275,622, which are incorporated herein by reference.

The actual function of delivering the graft may be accomplished by inflating a balloon of a catheter by introducing pressurized fluid into a lumen of the catheter from a source external to the patient. Inflation of the balloon applies a force to the graft and any attachment system supplied therein which extends radially and presses the graft and attachment system into the vessel wall just above and just below the aneurysm. When an attachment system is used, disengagement of the catheter from the graft also has been accomplished by taking advantage of the chemical properties of the material from which the attachment system is manufactured. For example, a prior art attachment system may be in the form of a coil of a nickel-titanium alloy, available under the trademark "NITINOL", that will expand radially upon being heated to a higher temperature. The longitudinal dimension of any attachment system used must account for any reduction in length that might result from radial expansion of the device. Other devices used to attach a graft to the aortic wall for AAA repair include intravascular stents of the type found in U.S. Pat. No. 4,733,665.

In order for a stent to be used most advantageously with a graft deployment system for treatment and repair of aneurysms, it is desirable for the stent to be composed of a biocompatable material, and to be simultaneously flexible enough to comply with the catheter or other element used to route the graft through the often tortuous vascular path to the site of the aneurysm and strong enough radially to maintain patency of the opening in the graft once delivered. The stent should be well suited to deployment by a delivery system that is not overly complex, and is reliable and easy to operate. Further it is desirable that the stent be expandable, so that upon application of a force or physical change from within sufficient to cause its radial expansion, it encourages affixation of itself and the graft to the aortic walls. Although various graft delivery systems have been proposed, none adequately provides all of the desirable features.

Proper anchoring of a stent for treatment of endovascular abdominal aortic aneurysm (AAA) is essential for securing a graft. Heretofore, exact placement of an anchoring stent with anchors located solely at one part of the stent was critical for properly securing the stent for repairing the abdominal aortic aneurysm. In addition, it is possible for the area of the aorta where anchoring barbs of such a stent were deployed to be not healthy enough to properly secure the entire device. It is also desirable for a multi-anchor stent to have anchors or barbs that present as small as possible of an increase in the insertion diameter of the unexpanded stent to provide a low profile during placement in the abdominal aortic aneurysm.

What has been needed and has been heretofore unavailable is a stent for use in combination with a graft which has a high degree of flexibility for efficient advancement through tortuous passageways, which can be radially expanded from a relatively small insertion diameter (low profile) to a relatively large diameter without substantial longitudinal contraction, and which exhibits mechanical strength sufficient to adhere to the vessel walls and to maintain the patency of a synthetic graft implanted at the site of an aneurysm. The present invention meets these needs.

SUMMARY OF THE INVENTION

Briefly, and in general terms, the present invention provides for a multiple-anchor stent for use with catheter-graft delivery systems for repairing diseased or injured vessels, and most notably for treating aneurysms, especially aneurysms of the abdominal aorta. The multiple-anchor stent provides a plurality of barbs throughout the entire circumference of the stent that face partially outwardly when the stent is in an expanded condition, so that exact placement of the anchors is less critical, and making it more likely that the stent will be anchored in healthy tissue, allowing the stent to be properly anchored in the abdominal aortic aneurysm. The large number of barbs on the multiple-anchor stent also allows the barbs to be made smaller, reducing the insertion diameter of the stent, while still providing effective anchoring. The multiple-anchor stent of the invention is expandable, so that a low profile can be maintained while the graft-and-stent combination is being routed to the aneurysm, and then expanded at the time of deployment to a diameter roughly approximating the diameter of a healthy abdominal aorta and the final diameter of the tubular-shaped graft. The multiple-anchor stent of the present invention has a configuration that allows the stent to expand radially to a much larger diameter than was heretofore possible, and is provided with hooks or barbs along the entire circumference of the stent to penetrate the aortic wall at least above the aneurysm to help ensure that the graft is anchored in healthy tissue. The multiple-anchor stent is somewhat flexible along its longitudinal axis to facilitate delivery to the treatment site through tortuous blood vessels, but in the expanded condition the multiple-anchor stent is sufficiently stable radially to maintain the patency of the graft and aorta and to attach the combined structure to the aortic walls.

As used herein, the term "proximal" refers to a location near a point of reference outside the patient, such as an origin or a point of attachment of a catheter, and the term "distal" refers to a location away from the point of reference outside the patient, such as near the portion of the catheter, stent or graft farthest away from the point of reference outside the patient.

The invention accordingly provides for an intravascular multi-anchor stent for implanting in a body lumen. The multi-anchor stent includes a plurality of cylindrical elements that are substantially independently expandable in the radial direction and that are interconnected so as to be generally aligned on a common longitudinal axis, and a plurality of the cylindrical elements has at least one barb that faces partially outwardly when the multi-anchor stent is in an expanded configuration for attaching the stent to the body lumen. In a currently preferred embodiment, each of the cylindrical elements has a plurality of barbs that face partially outwardly when the multi-anchor stent is in an expanded configuration for attaching the stent to the body lumen. In another preferred aspect of the invention, each of the barbs faces in alignment with the common longitudinal axis when the multi-anchor stent is in an unexpanded configuration. A plurality of connecting elements are provided for interconnecting only the cylindrical elements that are adjacent to each other so that the stent, when expanded in the radial direction, retains its overall length without appreciable shortening. In a preferred aspect of the invention, the plurality of connecting elements between adjacent cylindrical elements are in axial alignment. In one currently preferred embodiment, the cylindrical elements can be formed from a single piece of tubing, and in another currently preferred embodiment, the cylindrical elements are formed from a flat sheet of material that can be rolled into a cylindrical configuration from the flat sheet of material. In another preferred aspect of the invention, when made from a flat sheet of material, the flat sheet of material can have a first longitudinal support bar and a second longitudinal support bar which mate when the stent is rolled into the cylindrical configuration, and the flat sheet of material can have a first longitudinal edge with a plurality of first lap joints and a second longitudinal edge with a plurality of second lap joints, the first lap joints and the second lap joints engaging in a mating relationship when the stent is rolled into the cylindrical configuration. In a currently preferred embodiment, the multi-anchor stent is formed of a biocompatable material selected from the group consisting of stainless steel, tantalum, and thermoplastic polymers.

In one preferred embodiment, a multiple-anchor stent is attached to the distal end of a tubular graft such that at least a portion of the multiple-anchor stent is exposed distally beyond the distal end of the graft. The graft-and-stent are deployed intraluminally such that the multiple-anchor stent and the distal end of the graft are positioned distally of the aneurysm while the proximal end of the graft extends proximally of the aneurysm. The multiple-anchor stent is provided with a plurality of barbs along the length of the stent that face outwardly when the stent is in an expanded configuration for penetrating healthy tissue in the aortic wall in order to attach the graft-and-stent combination to the aortic wall.

Thus, in one embodiment, a pair of multiple-anchor stents can be attached to a tubular graft, one stent at the proximal end and one stent at the distal end of the graft. The stents can be oriented so that when both the graft and the stents are expanded to larger diameter states, the stents will be coaxial with the graft. The cylindrical elements of the stent are provided with anchors for penetrating healthy tissue in the walls of the aorta above and below the aneurysm, as well as along at least a portion of the length of the graft, to aid in attaching the combined structure to the aortic wall. The anchors can be barbs, and can be of various shapes, containing one or more angles, so that the anchors effectively will anchor the graft-and-stent combination to the aortic wall.

The graft-and-stent combination can be readily delivered to the aneurysm by mounting it on a balloon portion of a delivery catheter, and passing the catheter-graft-stent assembly through the vasculature to the implantation site. A variety of means can be used for securing the graft-and-stent combination to the catheter during delivery. Presently, it is preferred to compress the stent onto the balloon and retain the stent on the graft on the balloon using a protective sheath.

These and other aspects and advantages of the invention will become apparent from the following detailed description, and the accompanying drawings, which illustrate by way of example the features of the invention.

BRIEF DESCRIPTION OF THE DRAWINGS

FIG. 2 is a perspective view of a portion of the stent of FIG. 1 rolled into a cylindrical configuration;

FIG. 3 is an enlarged partial plan view of the stent of FIG. 1;

FIG. 8 is an elevational view, partially in section, of a pair of multi-anchor stents incorporated into a graft and a delivery system to deliver and deploy the stents and graft;

FIG. 9 is an elevational view, partially in section, of the multiple-anchor stent, graft and delivery system of FIG. 8 after the graft-and-stent combination has been advanced and deployed in the region of an aneurysm and the stents have been deployed;

FIG. 10 is an elevational view, partially in section, of the graft-and-stent combination of FIG. 8 after the combination has been deployed and the catheter withdrawn;

FIG. 11 is an elevational view, partially in section, of another means by which a stent according to the invention can be incorporated into a graft delivery system, depicting the system prior to advancement of the graft-and-stent combination into the region of an aneurysm;

FIG. 12 is an elevational view, partially in section of the delivery system of FIG. 11 after the graft-and-stent combination has been advanced and partially deployed in the region of an aneurysm;

FIG. 13 is an elevational view, partially in section, of an alternate means by which a stent according to the invention can be incorporated into a graft delivery system, depicting prior to deployment of the graft-and-stent combination;

DETAILED DESCRIPTION OF THE PREFERRED EMBODIMENTS

Exact placement of an anchoring stent with anchors located solely at one part of the stent was heretofore critical in properly securing the stent for repairing an abdominal aortic aneurysm. It is also possible that the area of the aorta where anchoring barbs would conventionally be deployed would not be healthy enough to properly secure the entire device.

Figure 1:
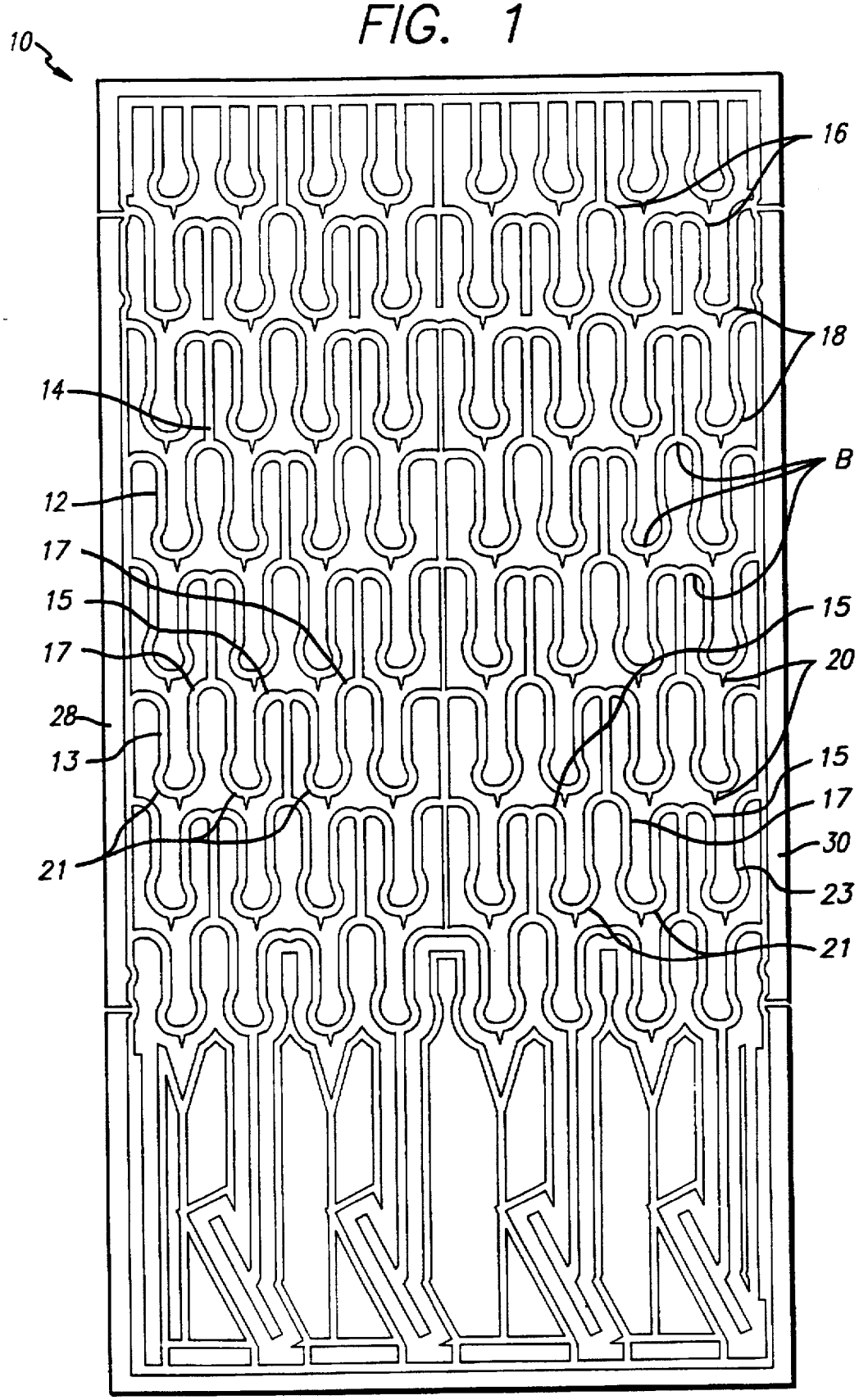
FIG. 1 is a plan view of a multiple-anchor stent prior to rolling into a cylindrical configuration.
Figure 4:
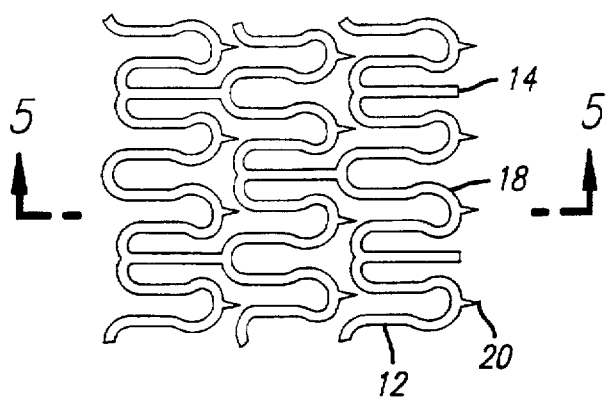
FIG. 4 is a plan view of a portion of the stent of FIG. 1 in an unexpanded configuration.
Figure 5:
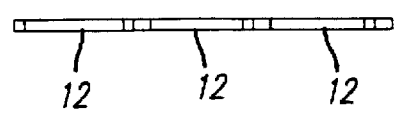
FIG. 5 is an elevational view of the portion of the stent taken along line 5—5 of FIG. 4.
Figure 6:
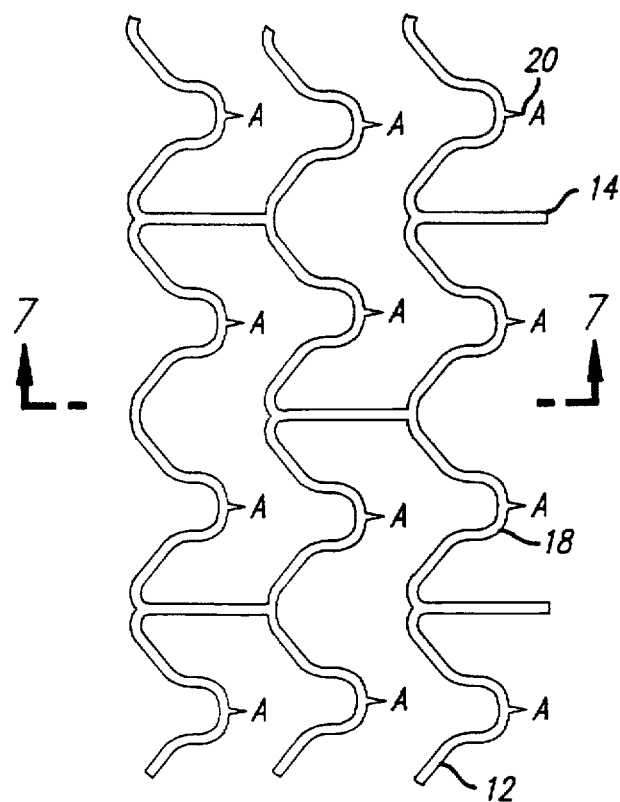
FIG. 6 is a plan view of a portion of the stent of FIG. 1 in an expanded configuration.
Figure 7:
FIG. 7 is an elevational view of the portion of the stent taken along line 7—7 of FIG. 6.

With reference to the drawings provided for illustrative purposes, the invention accordingly provides for an intravascular multiple-anchor stent for use with catheter-graft delivery systems for repairing diseased or injured vessels, and most notably for treating aneurysms, especially aneurysms of the abdominal aorta. With reference to FIGS. 1–7, in a currently preferred embodiment, an intravascular multiple-anchor stent 10 according to the invention generally comprises a plurality of cylindrical rings 12 that are spaced closely enough together to allow the stent to provide a reliable means of attaching a graft at the treatment site, but are not so tightly spaced as to inhibit the flexibility of the combination. As illustrated in FIG. 1, multi-anchor stent 10 includes a first type of cylindrical ring 13 having one W-shaped portion 15 interconnected between two U-shaped portions 17 by bulbous arched portions 21, and a second type of cylindrical ring 23 having one U-shaped portion 17 interconnected between two W-shaped portions 15 by bulbous arched portions 21. The cylindrical rings of the first and second types are alternately connected together by connecting members 14 that extend between W-shaped portions 15 and U-shaped portions 17. Each cylindrical ring typically has a serpentine configuration or wave pattern, having a series of alternating peaks 16 and valleys 18. The degrees of curvature indicated by arrows B along adjacent peaks and valleys are different. Attachment elements or anchors 20, shown in FIG. 1 in the form of barbs, can be provided on the ends of a plurality of the outwardly facing arches of valleys 18 in the rings that rotate outwardly when the stent is expanded, to engage with the aortic wall when the stent is deployed, so that each of a plurality of cylindrical elements has at least one barb that faces partially outwardly when the multi-anchor stent is in an expanded configuration for attaching the stent to the body lumen. In a currently preferred embodiment, as is illustrated in FIG. 1, each of the cylindrical elements has a plurality of barbs that face partially outwardly when the multi-anchor stent is in an expanded configuration for attaching the stent to the body lumen. As is shown in FIG. 1, the configuration of the barbs is preferably such that a barb is placed on each outwardly facing arch of the valleys 18, so that in a currently preferred embodiment, the stent currently has eight valleys per ring, providing eight anchors per ring.

The expansion properties of stainless steel make it a preferred material for the stent 10. As is described more fully below, the stent, including the barbs 20, can be formed from a flat sheet of material by chemically etching, laser cutting, or electronic discharge machining (EDM), and the like. It is also contemplated that the barbs can be formed independently of the stent and subsequently attached to it by welding, brazing or another process with the equivalent effect. The body of the stent has a width W and a length L, such that the length will be parallel with the longitudinal axis a of the stent when the body of the stent is rolled into a cylinder. To secure the stent in a configuration as a cylinder, the lengthwise edges 28 and 30 of the stent body shown in FIG. 1 can be connected with a suitable means such as by welding, brazing, soldering or with adhesives. A YAG laser is particularly suitable for welding lengthwise edges 28,30 together to form the body of the stent in a cylindrical configuration illustrated in FIG. 2.

In a presently preferred embodiment, it is contemplated that a stent with the dimensional characteristics described below would be suitable for use with a graft in AAA procedures, with a variety of vascular anatomies. It is clear, however, that a stent with other dimensions might be equally useful in a graft delivery procedure. Preferably, stent 10 is formed from a flat sheet of stainless steel. For a flat sheet, prior to being rolled into a cylindrical shape, width W of the stent can be approximately 0.63 inches (16 mm), while length L of the stent can be in the range of about 0.2 inches to about 2.0 inches (5.1 to 50.8 mm). It is desirable for connecting members 14 to have a transverse cross-section similar to the transverse dimensions of the serpentine or undulating components of the expandable rings or bands. The maximum width at the base of each anchor or barb is typically about 0.012 inches (0.30 mm), and the length of the shaft of each anchor or barb is typically about 0.020 inches (0.51 mm). As stated, these dimensions are preferred, but the selection of the most appropriate dimensions in a particular clinical situation may vary considerably from patient to patient.

After the stent 10 has been rolled and joined in a cylindrical configuration from a flat sheet, the stent can be uniformly expanded in a radial direction, both to a significant degree and without large variation in the level of diametric expansion of each cylindrical ring. The cylindrical rings 12 are transverse to the longitudinal axis A of the finished stent, and the varying degrees of curvature B between peaks 16 and valleys 18 tend to equalize the stresses experienced by the stent during expansion, so that the peaks and valleys of each band deform radially with substantial uniformity upon application of an expansion force. The unique structure of the stent permits the stent to increase from an initial, small diameter to any number of larger diameters. When the interconnections 14 between adjacent cylindrical rings are aligned with other interconnections between the other cylindrical rings, such that the interconnections traverse the distance between the peaks 16 of consecutive cylindrical rings. Each of the barbs also preferably faces in alignment with the common longitudinal axis when the multi-anchor stent is in an unexpanded configuration. This manner of connection of the cylindrical rings by interconnections 14 thus constrains shortening or contraction of the stent along its longitudinal axis during radial expansion about longitudinal axis A. This configuration also limits twisting of the stent upon expansion, and enhances more uniform expansion. The in-phase cylindrical ring patterns further are believed to reduce the likelihood that the stent or any portion of it will recoil, or collapse back to its starting diameter after deployment.

The number and orientation of interconnecting members 14 can be varied in order to maximize the desired longitudinal flexibility of the stent structure both in the unexpanded and in the expanded condition. Flexibility is advantageous during deployment of the graft and stent because it improves the ease and safety with which the combination can be delivered through the vascular system to the aneurysm. Following affixation of the stent to the aortic wall, longitudinal flexibility minimizes alteration of the natural physiology of the aorta due to the implant and helps to maintain compliance of the portions of the vessel supporting the graft. The discrete rings also have the capacity to rotate slightly with respect to each other without causing any significant alteration of the basic cylindrical structure of the stent. Accordingly, the cylindrical rings and connections cumulatively result in a stent that is very flexible along its length or longitudinal axis, but which provides uniform expansion and is very stable and resistant of collapse. The reticulated structure supplied by the patterning allows for the perfusion of arterial blood into the region of the aortic wall to which the portion of a stent extending beyond the graft is attached to anchor the graft in place. Such perfusion promotes assimilation of the synthetic prostheses by the aorta, and more generally, healing of the treated site.

The more uniform radial expansion of this design results in a stent 10 that can be expanded to a large diameter without substantial out-of-plane twisting, because no high stresses are concentrated in any one particular region. Rather, the forces are evenly distributed among the peaks and valleys, allowing the cylindrical rings to expand uniformly. Minimizing the out-of-plane twisting experienced by the stent during delivery and deployment of the graft-and-stent combination also carries with it the benefit of minimizing the risk of thrombus formation. The special expansion characteristics of the stent of the invention also allow any portion of the stent that extends distally or proximally of the graft to continue to expand even when the graft has achieved its maximum cross-sectional dimension, so as to more securely affix the graft-and-stent combination to the vessel above and below the aneurysm.

The uniformity in stress distribution further reduces the likelihood that fractures in the stent will occur due to stresses applied to any particular region or cylindrical ring of the stent. This feature also contributes to the ability of the stent to be expanded to a greater degree and at a faster rate than was feasible previously with other designs. Radial strength is not sacrificed upon expansion and the degree to which expansion causes longitudinal contraction, and thus a shortening of the stent, is minimal.

In keeping with the invention, it should be recognized that the attachment elements or anchors 20 can be provided in a variety of shapes and configurations other than barbs to insure adequate attachment of one or more stents, and to allow assimilation of the stent into the aortic wall of the aorta through endothelial tissue growth while the healing process is taking place.

Details of the various processes by which the stainless steel stent can be manufactured can be found in co-pending U.S. Ser. Nos. 08/175,214 and 08/164,986, which hereby are incorporated herein in their entirety by reference. Briefly, the stainless steel stent can be formed by a chemical etch process out of a flat sheet or a piece of tubing. The areas of stainless steel to remain are identified by covering the regions with a material resistant to the chemicals used in the etching process, such that when the metal is exposed to the chemicals, the openings or reticles in the patterned structure are created by reaction of the chemicals with the unprotected areas of the steel. The etching process develops smooth openings in the sheeting or tubing devoid of burrs or other artifacts that can be characteristic of other processes when products of the small sizes contemplated here are manufactured. An electropolishing process may be used after the chemical etching is complete in order to polish the stent surface. The stent surface can be polished to an approximately 5 to 10 micro inch finish.

There are numerous advantages in chemically etching a flat sheet of material, such as stainless steel, into the stent of the present invention. For example, chemical etching is economical since a large number of stents can be chemically etched on the same flat sheet at the same time. The chemical etching process creates no burrs and the surface finish of the eventual inside diameter of the stent can be improved by electro-polishing on one side only. Further, chemical etching creates no extra heat treating to the parts that are being processed. The raw material wall thickness and grain structure is more uniform in a flat sheet as opposed to chemical etching a stainless steel tube. Further, in a flat sheet, the bevel of the etching can be controlled, whereas when tubing is etched, the bevel creates a thicker part on the inside diameter and a thinner part on the outside diameter.

An important advantage of chemical etching the stent of the present invention from a flat sheet of stainless steel material is that a process known as "step etching" can be used. For example, by using step etching in the areas of the attachment elements or barbs 20 in FIG. 3, it is possible to remove portions of material so that the barbs will bend outwardly when the stent is expanded. In other words, step etching allows for the removal of material in highly selective areas so that upon radial expansion of the stent, areas having less material will have a tendency to bend or distort, such as with the barbs bending outwardly to engage the aortic wall.

Photo-lithographic techniques also can be employed for the manufacture of the stents, using a computer-controlled laser patterning process to remove the chemically resistive coating applied to the metal sheet or tube. A plurality of stents can be formed from one length of sheeting or tubing, by repeating the stent pattern and providing small webs or tabs to interconnect the stents. After the etching process, the stents can be separated by severing the small webs or tabs. Subsequently, if the stents were formed on a sheet, the individual stents are rolled and the edges welded together to provide a cylindrical configuration. Yet another method of making the stent of the present invention is by the commonly known process of electronic discharge machining (EDM). Using EDM, the stainless steel stent can be formed from a flat sheet or from a section of tubing.

In one preferred method of making stent 10, a laser is used to cut the stent 10 and anchors 20 out of a flat sheet or piece of stainless steel tubing. The laser settings can vary widely depending on the material, the shape of the stent being cut, and the end use. the laser cutting method described in U.S. Ser. No. 08/233,046, entitled "Method and Apparatus For Laser Cutting Small Objects," which is copending, is particularly instructive as to the manufacturing method of making stent 10 using a laser.

When stent 10 of the present invention is made from a material that is difficult to detect under fluoroscopy, such as stainless-steel, it is desirable to incorporate radiopaque markers to identify the position of the graft-and-stent assembly during deployment. The stent 10 of the present invention can be coated with a metal film that is radiopaque, such as gold, silver, platinum, tantalum and the like. One method of coating the stent of the present invention with a radiopaque marker is disclosed in copending U.S. Ser. No. 08/233,046 which is incorporated herein by reference.

One preferred method of incorporating the stent of the present invention into a graft delivery system is illustrated in FIGS. 8–10. Delivery system 50 is used to deploy tubular graft 52 at the site of abdominal aortic aneurysm 54 via stents 56 and 58. The structure of stents 56 and 58, the materials from which the stents are made, and the processes that might be used to form the stents are set forth in detail in connection with the discussion of FIGS. 1–7. It is contemplated that this use of the stent could be accomplished with a wide variety of graft types including well known tube grafts and bifurcated grafts. Due principally to the ability of the stent of the invention to expand from a very small diameter to a much larger diameter without substantial shortening, a relatively short length can be used. The graft system is sized so that its cross-section substantially matches that of the healthy portion of the aorta.

Delivery system 50 includes multilumen catheter 60 of the type used in other percutaneous procedures for deploying stents and other prostheses to repair portions of blood vessels. The catheter has a first lumen extending along its length which is in communication with two expandable members or balloons disposed at the distal end of the catheter. The balloons are spaced apart for a distance that is slightly less than the length of the shortest graft intended to be deployed using the system. Pressurized fluid or gas can be introduced into the balloon lumen to inflate the balloons, to exert an outward radial force on anything disposed about the balloon.

After stents 56 and 58 have been attached to graft 52, the graft-and-stent combination is loaded onto the distal end of catheter 60. The combination is positioned so that each stent overlies a balloon 62 and the graft rests over and is substantially coaxial with the portion of the catheter that is between the two balloons. In order to insure that the graft and stents remain in this position until the deployment function is accomplished, the two stents are compressed or "crimped" onto the balloons prior to insertion of delivery system 50 into the patient. The graft and stents also can be secured by positioning the stents between ridges or collars provided on the expandable members, which will restrain lateral movement of the combination. Alternatively, biodegradable adhesives might be used to temporarily affix the stents to the balloons, the adhesives being subject to degradation and absorption by the body when it is desired to deploy the graft.

Catheter 60 further is provided with sheath 64 that helps to hold the graft and stents onto the catheter and which prevents direct contact of the elements of the combination with the walls of the vessels while the system is being advanced to the treatment site, thus protecting the vascular system of the patient from any sharp edges on the stents. Rod or wire 66 or other suitable mechanical element is connected to the sheath and extends proximally along the length of the catheter so that it can be manipulated by the physician exterior to the patient and retracted (proximally) at the time of deployment. Alternatively, a sheath can be provided that traverses the entire length of the catheter, and can be retracted (proximally) from outside the patient to expose the graft-and-stent combination.

The catheter has a second lumen through which guidewire 68 passes. The guidewire advantageously is advanced through the vasculature of a patient beyond the site of aneurysm 54 as a preliminary step in the graft delivery procedure. After the guidewire has been positioned, the catheter carrying the graft and stents is advanced over the guidewire. Although a particular form of catheter has been described to route the graft-and-stent combination to the aneurysm, it will be apparent to those skilled in the art of treating aneurysms and similar conditions and of percutaneous catheter design that catheters of various configurations or wires and rods or the like could be used successfully to perform the same function. For example, well known fixed wire and rapid exchange wire systems also can be used in the delivery system described herein.

Attachment elements or barbs 20 are provided along the length of stent 58, which ultimately will attach the graft-and-stent combination to regions in the intima or aortic wall. The barbs anchor the stents and the graft while the implantation process is on going, and before the body has naturally assimilated the combination through intergrowth of endothelial cells. Stent 56 and stent 58 can be affixed to an end of graft 52 by staples. Other appropriate means might be used, such as a biocompatable adhesive, for example an epoxy resin, to attach stents 56,58 to graft 52. Alternatively, the stent might be sewn onto the graft at selected points. At least a portion of stents 56,58 extend out of graft 52, and if the stents and graft are joined by a butt joint, then substantially all of the stent will extend out of the graft.

In FIG. 8, all of the elements of graft delivery system 50 except the distal end of guidewire 68 are shown positioned proximally of aneurysm 54, before graft 52 and stents 56 and 58 have been deployed. Sheath 64 of catheter 60 covers the graft and stents disposed about balloons 62, and the distal end of the guidewire has entered the region of the aorta that is affected by the aneurysm. In FIG. 9, the sheath is withdrawn (proximally) exposing the graft-and-stent combination and the catheter is advanced so that the graft-and-stent combination span the aneurysm. The balloons 62 are inflated by the pressurized fluid or gas source external to the patient, and the radial forces accompanying expansion of the balloons are applied to expand both the graft and the stents radially outward, pressing both elements against aortic wall 72 proximal to and distal to the aneurysm. Barbs 20 provided on the stent 58 become embedded in the aortic wall 72, to anchor the graft-and-stent combination against downstream arterial pressure while the healing process takes place. In FIG. 10, the delivery apparatus has been withdrawn and the graft-and-stent combination is in final position across the aneurysm and attached to healthy tissue in aortic wall 72. It should be understood that when tubular graft 52 is expanded it is not stretching or deforming but is simply opening from a closed diameter to an open and expanded diameter. The graft material is generally inelastic and can be made from any number of materials compatible with the body such as polyester fiber made from polyethylene terephthalate, sold under the trademark "DACRON" by DuPont, polytetrafluoroethylene sold under the trademark "TEFLON" by DuPont, and other suitable polymeric materials.

Another preferred method of incorporating a stent according to the present invention into a graft delivery system is illustrated in FIGS. 11 and 12. This embodiment differs from that shown in FIGS. 8–10 in that a single stent is used to anchor the graft in FIGS. 11–12 while two stents were used in FIGS. 8–10. A single stent is appropriate in the aorta where blood pressures can exceed 100 mm/Hg, which is enough force to hold the proximal end of the graft in place without the need for an anchoring stent on the proximal end of the graft.

Delivery system 80 (FIGS. 11–12) is shown in the abdominal aorta, just proximal to aneurysm 54. A single stent 82 is attached by its proximal end 24 to the distal end of graft 52 by staples, adhesive, or by sewing or other appropriate means as previously described. The graft-and-stent combination is mounted on catheter 60 and the stent is crimped or compressed onto balloon 62. Retractable sheath 64 covers and protects both the graft-and-stent combination during delivery through the vascular system until sheath 64 is withdrawn proximally to allow deployment of the combination. Barbs 20 extend from the most distal cylindrical element 12 to attach the graft and stent to aortic wall 72. As can be understood with reference to FIGS. 11 and 12, the stent is affixed to the distal end of the graft so that it substantially extends out of the graft, with the result being that radial expansion forces can be applied to the stent by inflating balloon 62 of catheter 60 and simultaneously applying expansion force to graft 52. The stent is expanded simultaneously with the graft to drive barbs 20 into aortic wall 72 in healthy tissue distal to aneurysm 54, to anchor the combination to the vessel.

Figure 14:
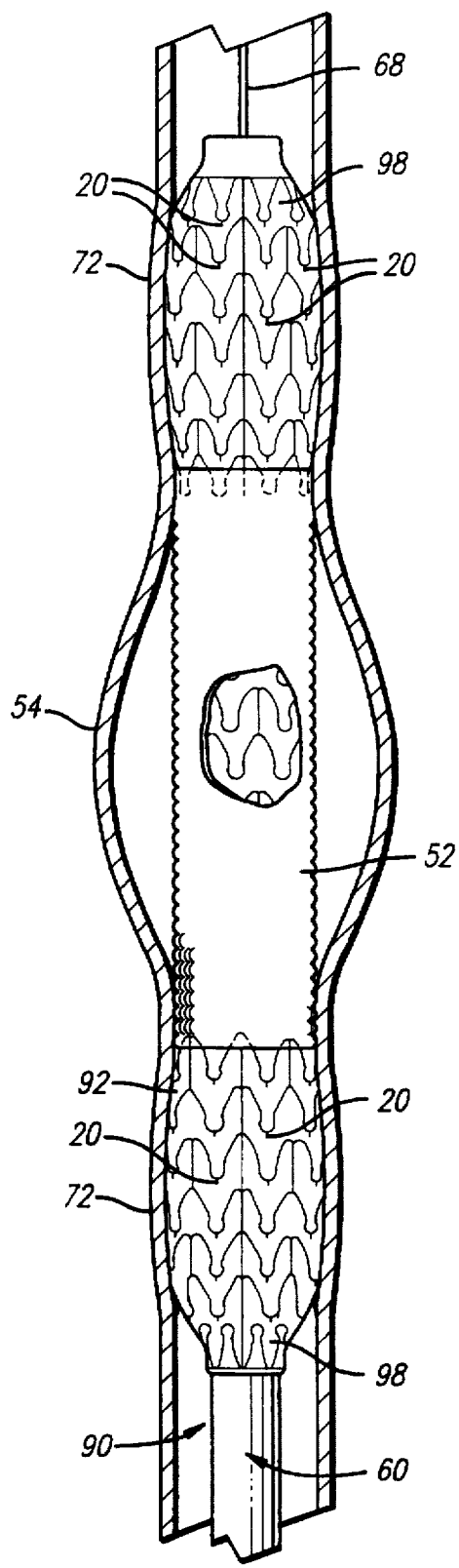
FIG. 14 is an elevational view, partially is section of the delivery system of FIG. 13, depicting the system during deployment of the graft-and-stent combination.

Another embodiment using the stent of the present invention in a graft delivery system is illustrated in FIGS. 13 and 14. Delivery system 90 includes stent 92 which is coaxial with and which extends the length of and beyond graft 52, such that first portion 94 of stent 92 extends proximally of graft 52 and second portion 96 extends distally of the graft. The cylindrical elements 12 of the first portion 94 and the second portion 96 of the stent 92 are equipped with barbs 20, as is shown more clearly and in greater detail in FIG. 1, which will be relied upon at the time of deployment to anchor the graft-and-stent combination to healthy aortic tissue while the prosthesis is accepted by the body of the patient.

Balloon 98 necessarily must have a much greater length when measured along a longitudinal axis of stent 92 than the balloons of previously described embodiments, because the stent of this embodiment is at least double the length of either of the two stents used in the preferred method of delivering the graft and of the stent used in the embodiments of FIGS. 8–12.

As can be seen with reference to FIG. 14, stent 92 and graft 52 which overlies it are positioned so that the graft spans the length of aneurysm 54. Balloon 98 then is inflated with pressurized fluid or gas to expand both the graft and the stent simultaneously and to force barbs 20 into engagement with aortic wall 72 distally of the aneurysm. The expandable member then is deflated and the delivery-system withdrawn leaving the graft-and-stent combination in place in the blood vessel.

Figure 15:
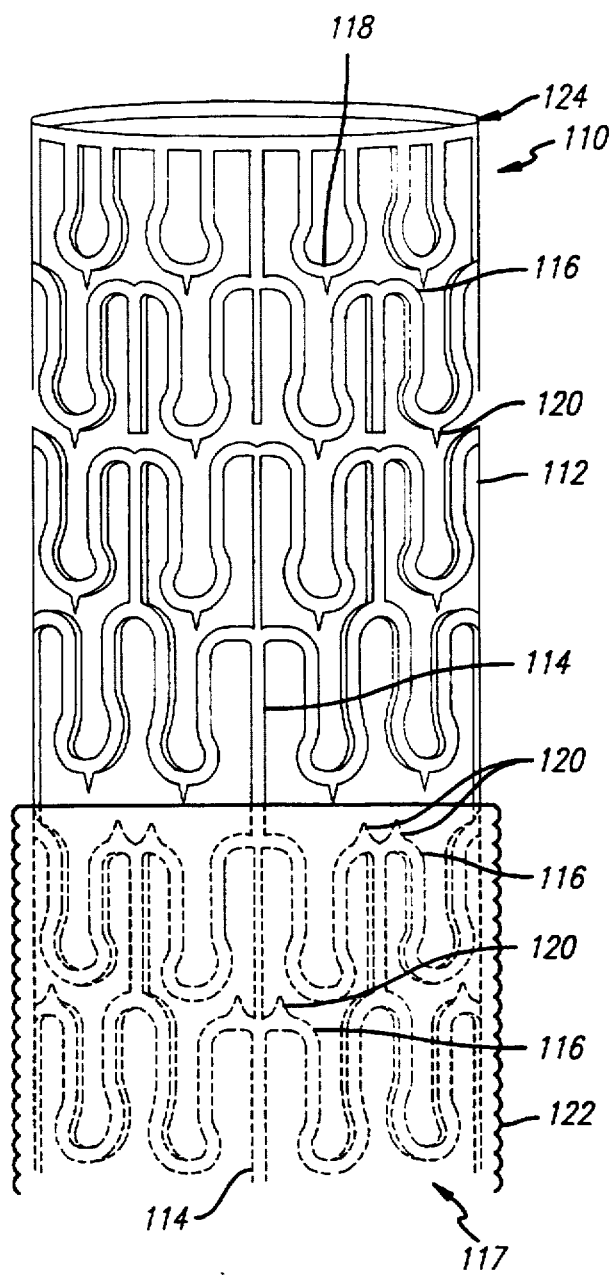
FIG. 15 is a perspective view of a portion of an alternative embodiment of a stent according to the invention having barbs at one end facing in one direction and barbs at the opposing end facing in the opposing direction.

With reference to FIG. 15, in an alternative embodiment of the intravascular multiple-anchor stent 110, the plurality of cylindrical rings 112 forming the stent are connected together by connecting members 114, and peaks 116 of at least one cylindrical ring at an end 117 of the stent to be secured within the graft 122 have barbs 120 that are pointed toward the longitudinal middle of the stent, away from the end 117 of the stent. Barbs 120 at the opposing end 124 of the stent to be secured to the vasculature are pointed toward the longitudinal middle of the stent in the opposing direction, away from end 124, so that the stent will simultaneously grip the vasculature and the graft to hold the graft and stent in place, relative to the vasculature.

Figure 16:
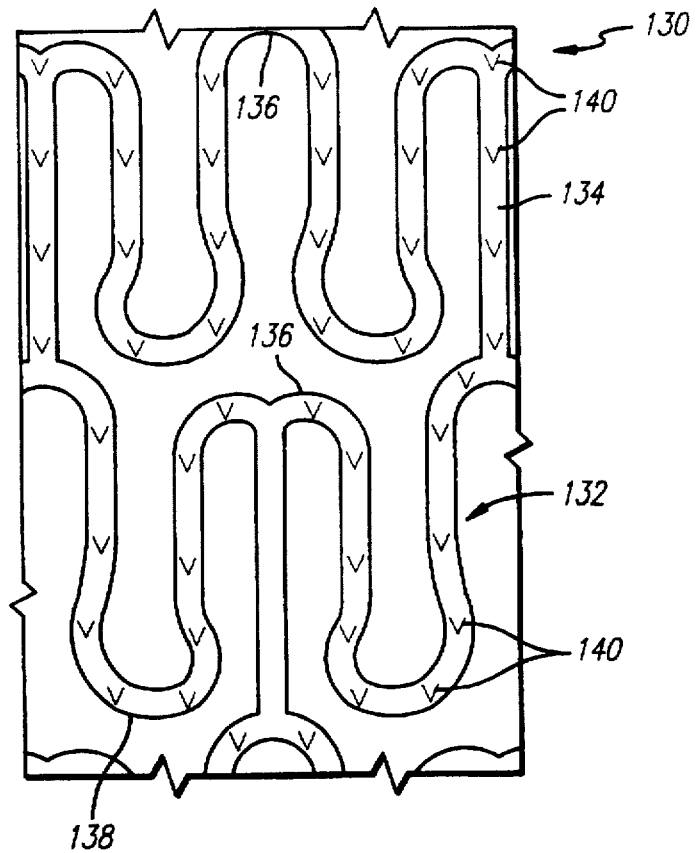
FIG. 16 is an enlarged partial plan view of an alternative embodiment of a stent according to the invention having a plurality of barbs on the surface of the peaks and valleys of the cylindrical elements of the stent.
Figure 17:
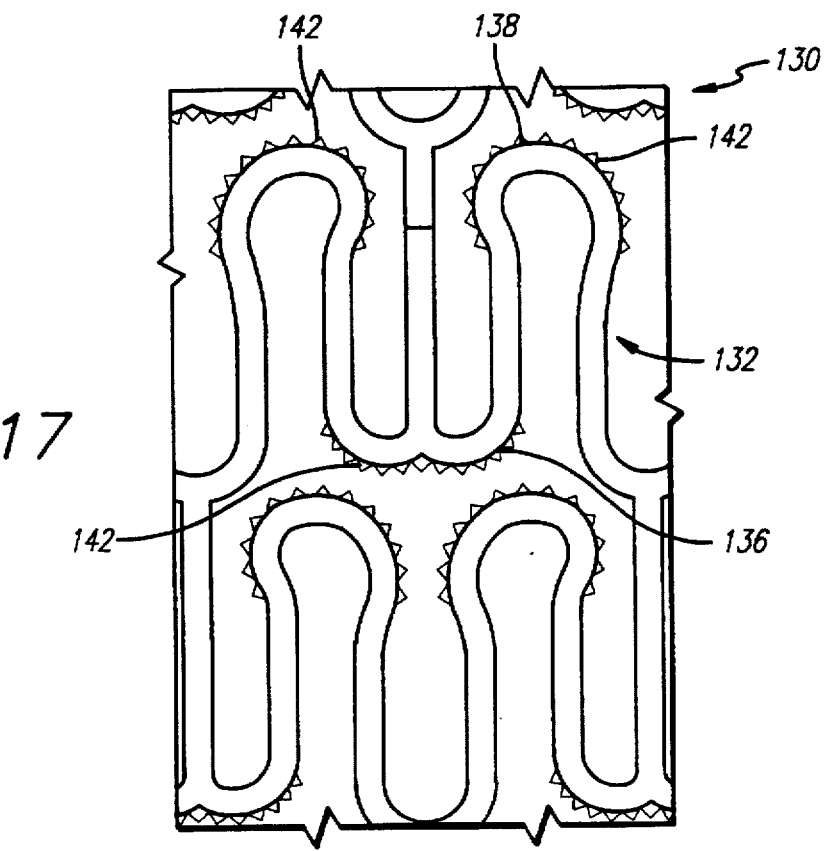
FIG. 17 is an enlarged partial plan view similar to that of FIG. 16 illustrating another alternative embodiment of a stent according to the invention providing a plurality of barbs on the outer edges of the peaks and valleys of the cylindrical elements of the stent.

In another alternative embodiment of a intravascular multiple-anchor stent 130 according to the invention, an enlarged portion of which is shown in FIG. 16, the surface of the stent can be covered with barbs 140 that can be formed in the surface of the cylindrical elements 132, including the surface of the peaks 136 and valleys 138 of the cylindrical rings 132, and the connecting members 134, to provide a sandpaper effect of raised, pointed, directional bumps of the surface of the stent. As is shown in FIG. 17, multiple barbs 142 also can be formed on the outer edges of the peaks and valleys of the cylindrical rings so that the barbs will be directed outwardly when the stent is expanded, to allow the stent to better grip whatever portion of the vasculature comes in contact with the stent.

While the invention has been illustrated and described herein in terms of its use as an endoprosthesis for implanting a graft to treat an aneurysm, it will be apparent to those skilled in the art that the stent can be used in other instances in other vessels of the body. Because the stent of the present invention has the novel features of attachment elements and the capacity to expand quickly from relatively small diameters to relatively large diameters, the stent is particularly well suited for implantation in almost any vessel where such devices can be used. This feature, coupled with the fact that the stent does not contract or recoil to any great degree after it is radially expanded, provides a highly desirable support member for other types of endoprosthesis.

In the foregoing description, statements concerning specific dimensions are given by way of example, and it should be apparent to one of ordinary skill in the art that other similar dimensions may also be suitable according to the principles of the invention. It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An intravascular multi-anchor stent for implanting in a body lumen, comprising:

a first cylindrical element which is substantially independently expandable in the radial direction, the first cylindrical element having a W-shaped portion interposed between two U-shaped portions, the W-shaped portion connected to the U-shaped portions by bulbous arched portions;

a pair of second cylindrical elements which are substantially independently expandable in the radial direction, each one of the pair of second cylindrical elements having a U-shaped portion interposed between two W-shaped portions, the U-shaped portion connected to the W-shaped portions by bulbous arched portions, the first cylindrical element interposed between the pair of second cylindrical elements so as to be generally aligned on a common longitudinal axis;

a barb disposed on at least some of the bulbous arched portions of the first and second cylindrical elements, the barb facing partially radially outwardly when the multi-anchor stent is in an expanded configuration to attach the stent to the body lumen;

a first interconnecting element interconnecting the W-shaped portions of the first cylindrical element to the U-shaped portions of a first one of the pair of the second cylindrical element; and a pair of second interconnecting elements interconnecting the two W-shaped portions of a second one of pair of second cylindrical elements to the U-shaped portions of the first cylindrical element.

2. The intravascular multi-anchor stent of claim 1, wherein each of the first and second cylindrical elements has a plurality of barbs that face radially outwardly when the multi-anchor stent is in an expanded configuration for attaching the stent to the body lumen.

3. The intravascular multi-anchor stent of claim 2, further comprising means for connecting the first and second cylindrical elements so that, when said stent is expanded in the radial direction, said stent retains its overall length without appreciable shortening.

4. The intravascular multi-anchor stent of claim 1, wherein each of the barbs faces parallel to the common longitudinal axis when the multi-anchor stent is in an unexpanded configuration.

5. The intravascular multi-anchor stent of claim 1, wherein each one of the first and second cylindrical elements has a plurality of barbs disposed on at least some of the bulbous arched portions of the first and second cylindrical elements.

6. The intravascular multi-anchor stent of claim 5, each one of the plurality of barbs faces substantially in the same direction when said stent is in said expanded configuration, to provide a directional gripping action.

7. The intravascular multi-anchor stent of claim 5, wherein said barbs of said first and second cylindrical elements at one longitudinal end of said stent face in a first direction, and said barbs of said first and second cylindrical elements at an opposing longitudinal end of said stent face in an opposing direction when said stent is in said expanded configuration.

8. The intravascular multi-anchor stent of claim 7, wherein said barbs at said one longitudinal end and at said opposing longitudinal end are pointed toward a longitudinal middle portion of said stent when said stent is in said expanded configuration.

9. The intravascular multi-anchor stent of claim 1 wherein plurality of barbs disposed on at least some of the bulbous arched portions of the first and second cylindrical elements comprise pointed bumps formed on an exterior surface portion of the first and second cylindrical elements.

10. The intravascular multi-anchor stent of claim 9, wherein each one of the pointed bumps faces substantially in the same direction when said stent is in said expanded configuration, to provide a directional gripping action.

* * * * *